US00PP19835P2

(12) United States Plant Patent
Hansen

(10) Patent No.: US PP19,835 P2
(45) Date of Patent: Mar. 17, 2009

(54) *HOSTA* PLANT NAMED 'SILK ROAD'

(50) Latin Name: *Hosta hybrida*
Varietal Denomination: Silk Road

(75) Inventor: Hans Andrew Hansen, Waseca, MN (US)

(73) Assignee: Shady Oaks Nursery LLC, Waseca, MN (US); Part Interest ( * ) Notice: Subject to any disclaimer, the term of this patent is extended or adjusted under 35 U.S.C. 154(b) by 0 days.

(21) Appl. No.: 12/070,018

(22) Filed: Feb. 14, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Annette H Para
*Assistant Examiner*—S. B. McCormick Ewoldt
(74) *Attorney, Agent, or Firm*—Penny J. Aguirre

(57) ABSTRACT

A new cultivar of *Hosta* named 'Silk Road', a chimeral mutation of *Hosta* 'Silk Kimono', characterized by its unique variegated foliage with deep green centers and wide creamy yellow to creamy white margins comprising about one half of the leaf area. 'Silk Road' has an upright plant habit of large broadly ovate leaves held horizontally on erect petioles and blooms with pale lavender flowers held on erect flower scapes in mid summer.

1 Drawing Sheet

Botanical classification: *Hosta hybrida.*
Cultivar designation: 'Silk Road'.

BACKGROUND OF THE INVENTION

The present invention, *Hosta* 'Silk Road', relates to a new and distinct cultivar of *Hosta,* botanically known as a *Hosta hybrida,* hereinafter referred to as 'Silk Road'.

The inventor discovered the new cultivar, 'Silk Road', in summer of 2004 in his garden in Waseca, Minn. 'Silk Road' originated as a naturally occurring chimeral mutation of *Hosta* 'Silk Kimono' (not patented).

Asexual reproduction of the new cultivar was first accomplished by the inventor utilizing in vitro propagation in Waseca, Minn. fall of 2006. Asexual reproduction of the new cultivar by division and tissue culture has shown that the unique features of 'Silk Road' are stable and reproduced true to type in successive generations.

SUMMARY OF THE INVENTION

The following traits have been repeatedly observed in trials in Minnesota for a period of three years and represent the characteristics of the new cultivar. These attributes in combination distinguish 'Silk Road' as a new and unique cultivar of *Hosta.*

1. The foliage of 'Silk Road' is variegated with deep green centers and wide creamy yellow to creamy white margins. The margin width ranging from 2 to 6 cm with the leaf margin comprising about one half of the leaf area.
2. 'Silk Road' has large broad leaves with an upright vase-shaped plant habit.
3. 'Silk Road' reaches a height of about 33 cm in height (excluding flower scapes) and about 81 cm in width.
4. 'Silk Road' blooms in mid summer with pale lavender flowers held above foliage on erect flower scapes.

In comparison to the parent plant, 'Silk Kimono', 'Silk Road' has leaf margins that are 2 to 3 times wider than 'Silk Kimono' and 'Silk Road' has an upright plant habit, whereas 'Silk Kimono' has a more mounded plant habit. 'Silk Road' can also be compared to 'Robert Frost' (not patented), 'Robert Frost' has leaves that are similar in size and variegation pattern and exhibits a similar plant habit, however the leaves 'Robert Frost' are blue-green in color and the margins are not as wide as those of 'Silk Road'.

BRIEF DESCRIPTION OF THE DRAWING

The accompanying colored photograph illustrates the distinct foliage characteristics of the new *Hosta.* The photograph was taken in July of a three year-old plant of 'Silk Road' as grown outdoors in Waseca, Minn. The colors in the photograph are as close as possible with the photographic and printing technology utilized the color values cited in the detailed botanical description most accurately describe the colors of the new *Hosta.*

DETAILED BOTANICAL DESCRIPTION OF THE PLANT

The following is a detailed description of three year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Blooming period.*—About 3 weeks from mid July to early August.

*Plant habit.*—Herbaceous perennial, clump-forming, upright habit.

*Height and spread.*—Reaches about 33 cm in height (excluding flower scapes) and about 81 cm in width.

*Hardiness.*—U.S.D.A. Zones 3 to 8.

*Culture.*—Light to full shade, moist soils of moderate fertility.

*Diseases and pests.*—No susceptibility or resistance to diseases or other pests has been observed.

*Root description.*—Freely branched, fleshy.

*Propagation.*—In vitro propagation is the preferred method utilizing typical methods for *Hosta,* division are also possible.

*Root development.*—Rooted transplants from tissue culture fully develop in a 96-cell liner in about 6 to 8 weeks in a greenhouse with average temperatures of about 70° F.

*Growth rate.*—Moderately vigorous.

Foliage description:

*Leaf shape.*—Broadly ovate.

*Leaf division.*—Simple.

*Leaf base.*—Broadly cuneate to truncate.

*Leaf apex.*—Acuminate.

*Leaf venation.*—10 to 11 pairs of veins, camptodrome pattern, impressed on upper surface and raised on lower surface, color matches leaf coloration.

*Leaf margins.*—Entire, wavy.

*Leaf attachment.*—Petiolate.

*Leaf arrangement.*—Basal, radiate spirally from base.

*Leaf surface.*—Glabrous on upper surface, slightly glaucous on lower surface.

*Leaf substance.*—Average.

*Leaf orientation.*—Held nearly horizontal on upright petioles.

*Leaf color.*—Spring foliage upper surface; centers 137A, margins 10D, intermediate area between the margins and centers 191B and small amounts of 144B and 144C, spring foliage lower surface; centers 191A, margins 8D, intermediate area between the margins and centers 191C and small amounts of 139D, 189C and 145B, summer foliage upper surface; centers 137A with intermediate areas of 189B and 144A and margins 11C to 11D, summer foliage lower surface; 189A with intermediate areas 189B and small amount of 144A and margins 11C to 11D.

*Leaf variegation pattern.*—Margins range from 2 to 6 cm in width, comprising about one half of the leaf area, center area has a primary area that is elliptic in shape with basal markings radiating out from the base on either side of the middle pattern.

*Leaf size.*—About 25 cm in length, about 19 cm in width.

*Leaf quantity.*—About 5 per shoot (eye).

*Petiole size.*—About 30.5 cm in length, about 1.5 cm in width.

*Petiole color.*—Spring foliage; inner surface 144A with stripes of 144B and a thin margin of 144D, outer surface 144D with wide margins of 139A and a thin margin of 144C, summer foliage; inner surface 137A blending in center with 144A and a thin margin of 11D, outer surface 144D blending with 144A and 137A near margin with margin 11D, surface is glabrous.

*Petiole surface.*—Glabrous.

*Petiole shape.*—Sulcate.

Flower Scape Description:

*Scape shape.*—Round, solid.

*Scape number.*—One per mature eye under normal growing conditions.

*Scape posture.*—Straight, erect.

*Scape size.*—Average of 89 cm in length, average of 6 mm in width.

*Scape color.*—144B.

*Scape surface.*—Slightly glaucous.

*Leafy bracts.*—None observed.

Flower Description:

*Inflorescence type.*—Terminal racemes of single bell-shaped flowers on elongated scapes.

*Lastingness of inflorescence.*—About 3 weeks from first opening bloom to fading of last opening bloom, individual blooms last about one day.

*Flower shape.*—Bell-shaped.

*Flower number.*—Average of 34.

*Flower internode length.*—Average of 5 mm, longer on basal region to tightly congested at terminal.

*Flower fragrance.*—None.

*Flower buds.*—Spathulate in shape, average of 4.3 cm in length and 1.5 cm in diameter, surface is glabrous and somewhat waxy, color at maturity N155D suffused with 85B to 85D.

*Flower size.*—About 7 cm in length and about 1.8 cm in diameter.

*Flower color.*—Emerges and matures to N155D suffused with 85C to 85D with tube region N155D.

*Pedicels.*—About 6 mm in length, 2 mm in diameter, 145C to 145D in color, glabrous texture.

*Perianth features.*—Comprised of 6 tepals, 3 interior and 3 exterior, overlapping and fused from the middle of the expanded region to base of tube.

*Tepals.*—Oblanceolate in shape, about 5 cm in length, about 1.2 cm in width, color of outer and inner surfaces N155D suffused with 85C to 85D with tube region N155D and thin stripes on inner surface of 85C, glabrous surfaces, entire margins, fused base, acute apex.

*Floral bracts.*—One per flower, broadly lanceolate in shape, average of 2.5 cm in length and 1 cm in width, color of upper and lower surface 144A with base and thin margin 144D, entire margin, truncate base (sessile to scape), glabrous surface.

Reproductive Organs:

*Gynoecium.*—1 Pistil, style is about 6 cm in length, 1 mm in width, extending abut 1.5 cm beyond perianth, and 155A in color, stigma is pillose, 1 mm in diameter and length and 155A in color, ovary is superior, about 7 mm in length and 3 mm in width, compound, composed of 3 locules, 145C in color.

*Androecium.*—6 stamens, filament is 155A in color, about 5.2 cm in length, 1 mm in width, length is equal to perianth length, anthers are 5 mm in length, 1.5 mm in width, attachment is versatile, 202A in color, dehiscence is longitudinal, pollen is abundant and 15B in color.

*Fruit and seed.*—No seed pod were formed when grown under garden conditions where normal seed set was observed for other *Hosta* hybrids.

It is claimed:

1. A new and distinct cultivar of *Hosta* plant named 'Silk road' as herein illustrated and described.

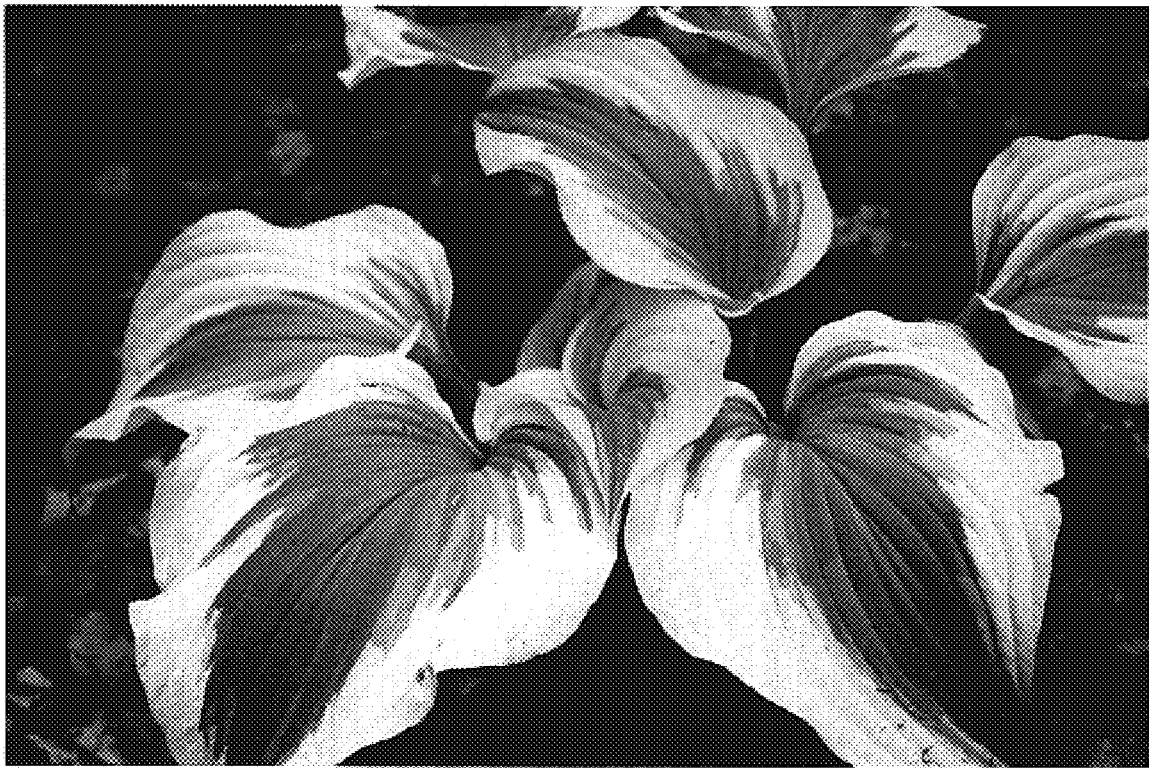

* * * * *